United States Patent
Mannello et al.

(10) Patent No.: US 11,318,171 B2
(45) Date of Patent: May 3, 2022

(54) METHODS AND COMPOSITIONS FOR IMPROVING SKELETAL MUSCLE PROTEIN FRACTIONAL SYNTHETIC RATE

(71) Applicant: MYOS RENS TECHNOLOGY INC., Cedar Knolls, NJ (US)

(72) Inventors: Joseph Mannello, Cedar Knolls, NJ (US); Neerav D. Padliya, Cedar Knolls, NJ (US); Maghsoud Dariani, Cedar Knolls, NJ (US)

(73) Assignee: MYOS CORP., Cedar Knolls, NJ (US)

( * ) Notice: Subject to any disclaimer, the term of this patent is extended or adjusted under 35 U.S.C. 154(b) by 144 days.

(21) Appl. No.: 16/876,666

(22) Filed: May 18, 2020

(65) Prior Publication Data

US 2020/0276247 A1 Sep. 3, 2020

Related U.S. Application Data

(62) Division of application No. 16/508,814, filed on Jul. 11, 2019, now Pat. No. 10,925,904.

(60) Provisional application No. 62/756,286, filed on Nov. 6, 2018.

(51) Int. Cl.
*A61K 35/57* (2015.01)
*A61K 45/06* (2006.01)

(52) U.S. Cl.
CPC .............. *A61K 35/57* (2013.01); *A61K 45/06* (2013.01)

(58) Field of Classification Search
CPC ................................ A61P 21/00; A61K 35/57
See application file for complete search history.

(56) References Cited

U.S. PATENT DOCUMENTS

| | | | |
|---|---|---|---|
| 8,815,320 B2 | 8/2014 | Buxmann et al. | A23B 5 015 |
| 2007/0275036 A1* | 11/2007 | Green, III | A23L 15/00 424/439 |
| 2020/0138873 A1 | 5/2020 | Mannello et al. | |

FOREIGN PATENT DOCUMENTS

CN 108606269 10/1918

OTHER PUBLICATIONS

Bish et al. "Long-term systemic myostatin inhibition via liver-targeted gene transfer in golden retriever muscular dystrophy" Human gene therapy 2011 22(12): 1499-1509.
Bogdanovich et al. "Functional improvement of dystrophic muscle by myostatin blockade" Nature 2012 420(6914): 418.
Brose et al. "Creatine supplementation enhances isometric strength and body composition improvements following strength exercise training in older adults" J Gerontol A Biol Sci Med Sci. 2003 58(1):11-9.
Chrusch et al. "Creatine supplementation combined with resistance training in older men" Med Sci Sports Exerc. 2001 33(12):2111-7.
Holzbaur et al. "Myostatin inhibition slows muscle atrophy in rodent models of amyotrophic lateral sclerosis" Neurobiology of disease 2006 23.3: 697-707.
Klimek et al. "Acute Inhibition of myostatin-family proteins preserves skeletal muscle in mouse models of cancer cachaxia" Biochemical and biophysical research communications 2010 391(3):1548-1554.
McPherron et al. "Regulation of skeletal muscle mass in mice by a new TGF-beta superfamily member" Nature 1997 387(6628):83-90.
Mithal et al. "Impact of nutrition on muscle mass, strength, and performance in older adults" Osteoporos Int. May 2013;24(5):1555-66.
Morley, J.E. "Pharmacologic Options for the Treatment of Sarcopenia" Calcif Tissue Int. Apr. 2016;98(4):319-33.
Murphy et al. "Acute antibody-directed myostatin inhibition attenuates disuse muscle atrophy and weakness in mice" Journal of applied physiology 2011 110(4):1065-1072.
https://iofbonehealth.org/treating-sarcopenia 2017.
International Search Report and Written Opinion in PCT/US2019/041279 dated Oct. 14, 2019.
Wilson et al. "The Effects of Fertilized Egg Yolk Isolates on Anabolic and Catabolic Signaling in Skeletal Muscle" The FASEB Journal Abstract No. 819.1 Apr. 1, 2015.
Office Communication dated Feb. 28, 2020 in U.S. Appl. No. 16/508,814 filed Jul. 11, 2019.
Office Communication dated May 1, 2020 in U.S. Appl. No. 16/508,814 filed Jul. 11, 2019.

* cited by examiner

*Primary Examiner* — Qiuwen Mi
(74) *Attorney, Agent, or Firm* — Licata & Tyrrell P.C.

(57) ABSTRACT

Methods and egg yolk powder containing compositions for improving skeletal muscle protein fractional synthetic rate (FSR) in mammals and inhibiting or reversing sarcopenia are provided.

6 Claims, 5 Drawing Sheets

METHODS AND COMPOSITIONS FOR IMPROVING SKELETAL MUSCLE PROTEIN FRACTIONAL SYNTHETIC RATE

This patent application is a divisional of U.S. patent application Ser. No. 16/508,814, filed Jul. 11, 2019, which claims the benefit of priority from U.S. Provisional Application Ser. No. 62/756,286 filed Nov. 6, 2018, the teachings of each of which are incorporated by reference in their entireties.

FIELD

Embodiments of the present invention are generally related to methods and compositions for improving skeletal muscle protein fractional synthetic rate (FSR) in mammals.

BACKGROUND

Muscle loss represents one of the most important causes of functional decline and loss of independence in older adults. Age-related muscle loss or sarcopenia is commonly observed in many older adults and is also characterized by a decrease in the rate of muscle protein synthesis. In addition, low muscle mass is associated with fall-related injuries which can be devastating to adults over the age of 60 years, particularly if they result in bone fractures.

Myostatin, first described in 1997, is a protein in the transforming growth factor β superfamily that is produced by myotubes and can act in an endocrine, autocrine, and paracrine fashion (McPherron et al. Nature 1997 387(6628): 83-90). Myostatin binds to a transmembrane receptor protein on myocytes, activin receptor type IIB, to inhibit the Akt-mTOR pathway, upregulate activity of the ubiquitin-proteasome pathway, and prevent synthesis of satellite cell replication and translocation (myoblast proliferation). Activation of these various pathways either inhibits muscle hypertrophy or promotes muscle atrophy. Inhibition of myostatin by various methods has been shown to interrupt these various pathways, reversing or preventing muscle atrophy in various rodent models of disease states, including disuse atrophy (Bogdanovich et al. Nature 2012 420(6914): 418; Holzbaur et al. Neurobiology of disease 2006 23.3: 697-707; Klimek et al. Biochemical and biophysical research communications 2010 391(3):1548-1554; Murphy et al. Journal of applied physiology 2011 110(4):1065-1072). Long-term myostatin inhibition by gene transfer therapy resulted in increased muscle mass in golden retrievers with muscular dystrophy (Bish et al. Human gene therapy 2011 22(12): 1499-1509).

Recommendations for preventing sarcopenia include exercise, in particular resistance training and adequate nutrition inclusive of protein balanced with non-acid producing foods fruits and vegetables. See https:// with the extension iofbonehealth.org/treating-sarcopenia of the world wide web.

Creatine supplements have been indicated to aid in muscle development for older adults that are following a resistance training program (Brose et al. J Gerontol A Biol Sci Med Sci. 2003 58(1):11-9; Chrusch et al. Med Sci Sports Exerc. 2001 33(12):2111-7).

Maintaining appropriate blood levels of vitamin D may also aid in maintaining muscle strength and physical performance (Mithal et al. Osteoporos Int. 2013 May; 24(5): 1555-66).

While high-dose testosterone increases muscle power and function, but has a number of potentially limiting side effects (Morley, J. E. Calcif Tissue Int. 2016 April; 98(4):319-33).

Other drugs in clinical development include selective androgen receptor molecules, ghrelin agonists, myostatin antibodies, activin IIR antagonists, angiotensin converting enzyme inhibitors, beta antagonists, and fast skeletal muscle troponin activators (Morley, J. E. Calcif Tissue Int. 2016 April; 98(4):319-33).

As sarcopenia is a major predictor of frailty, hip fracture, disability, and mortality in older adults (Morley, J. E. Calcif Tissue Int. 2016 April; 98(4):319-33), agents which inhibit and/or reverse sarcopenia are needed.

SUMMARY

An aspect of the present invention relates to a method for improving skeletal muscle protein fractional synthetic rate (FSR) in mammals. The method comprises administering to the mammal a composition comprising egg yolk powder.

In one nonlimiting embodiment, the mammal is an older adult.

In one nonlimiting embodiment, the composition administered is FORTETROPIN.

Another aspect of the present invention relates to a method for inhibiting or reversing sarcopenia in a mammal. The method comprises administering to the mammal a composition comprising egg yolk powder.

In one nonlimiting embodiment, the mammal is an older adult.

In one nonlimiting embodiment, the composition administered is FORTETROPIN.

DETAILED DESCRIPTION

Figure 1:
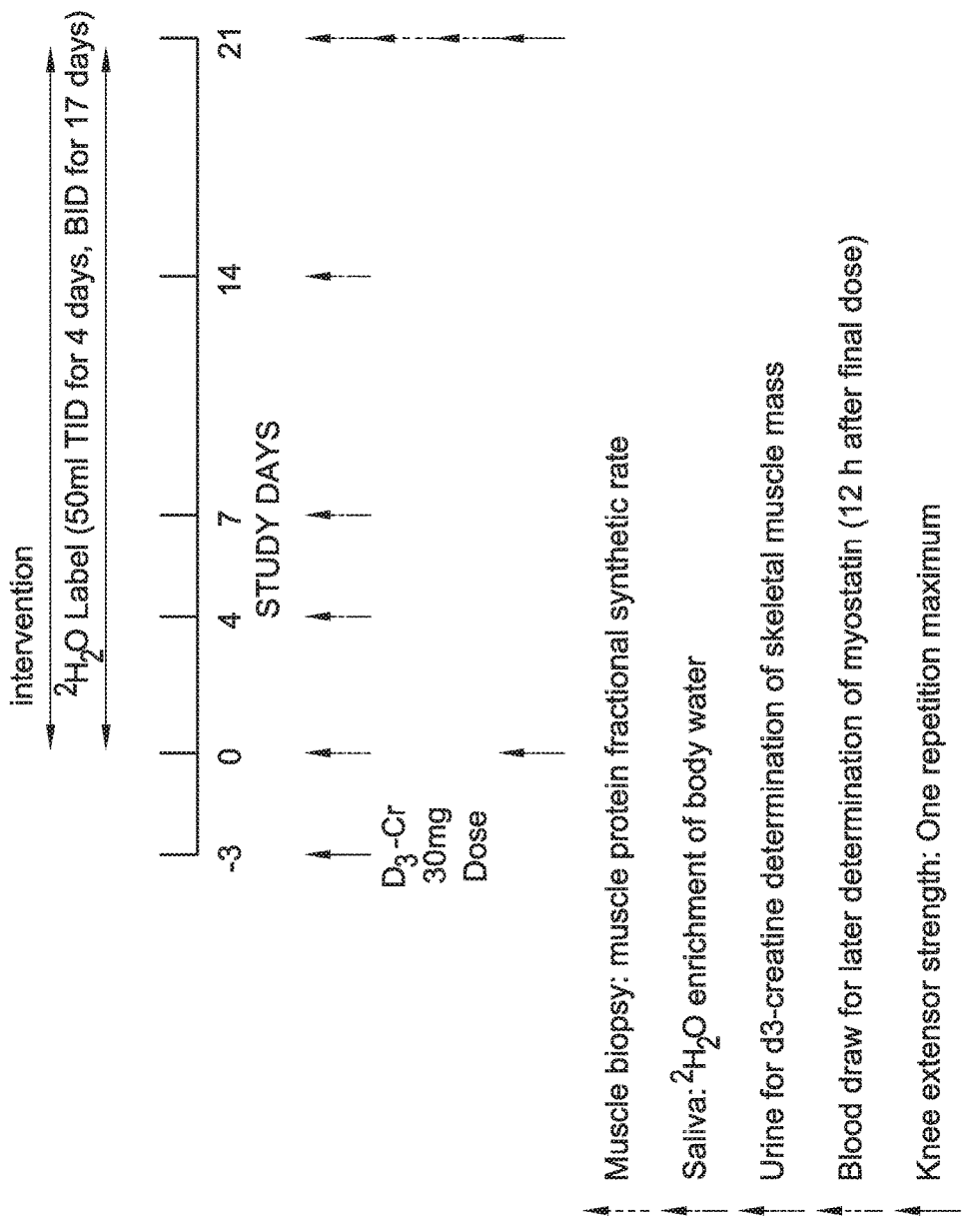
FIG. 1 provides a diagram of the design of a study showing the effects of FORTETROPIN on skeletal muscle protein FSR.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

The present invention provides methods and compositions for improving skeletal muscle protein fractional synthetic rate (FSR) in mammals. The methods comprise administering to the mammal a composition comprising egg yolk powder.

For purposes of the present invention, by the terms "improve", "improving" or "improvement" with respect to skeletal muscle protein fractional synthetic rate, it is meant an increase in synthesis of skeletal muscle proteins indicative of muscle growth.

Methods and compositions of the present invention are useful in inhibiting and/or reversing sarcopenia in mammals.

Compositions administered in accordance with the present invention comprise egg yolk powder or one or more proteins and/or lipids derived from egg yolk which are effective in growth and development of lean muscle tissue.

In one nonlimiting embodiment, the composition administered is FORTETROPIN. FORTETROPIN is a fertilized egg yolk derived product used as a dietary and nutritional supplement (MYOS RENS TECHNOLOGY INC. CORPORATION Cedar Knolls, N.J.). FORTETROPIN has been found to have an abundance of pro-angiogenic and host-defense proteins when compared to unfertilized egg yolk. When administered to humans and rats, FORTETROPIN has been shown to reduce serum myostatin levels and demonstrate a change in downstream signaling pathways supportive of muscle hypertrophy and resulting in an increase in lean body mass. FORTETROPIN may be produced via high pressure pasteurization (HPP) and freeze drying of at least a portion of an egg. A method for production of FORTETROPIN is disclosed in U.S. Pat. No. 8,815,320, teachings of which are herein incorporated by reference in their entirety.

In one nonlimiting embodiment, FORTETROPIN production is optimized to enhance potency as it relates to muscle disuse atrophy by modifying one or more egg yolk-related parameters such as, but not limited to, incubation time post-lay, fertility status and breed of chicken.

In another nonlimiting embodiment, the composition comprises an avian follistatin such as described in U.S. Published Patent Application No. 2007/0275036, the disclosure of which is incorporated herein by reference in its entirety and/or other proteins and/or lipids found in avian eggs and which are beneficial in growth and development of lean muscle tissue such as, but not limited to, those described in U.S. Provisional Application Ser. No. 62/755,601, the disclosure of which is incorporated herein by reference in its entirety.

For purposes of the present invention, when the phrases "egg yolk powder" or "composition comprising egg yolk powder" are used, they are meant to be inclusive, but are not limited to, egg yolk powder, one or more proteins and/or lipids derived from egg yolk which are effective in growth and development of lean muscle tissue, FORTETROPIN and avian follistatin.

By "mammal" or "mammals" it is meant to include, but is not limited to, humans, apes, monkeys, cows, sheep, goats, dogs, cats, mice, rats, and transgenic species thereof.

In one nonlimiting embodiment, the mammal is an older adult. In one nonlimiting embodiment, the older adult is age 60 or greater.

In one nonlimiting embodiment, the composition comprising egg yolk powder is administered orally on a daily basis, one, two or three times a day.

In one nonlimiting embodiment, the composition comprising egg yolk powder is administered in an amount effective to upregulate mTor pathway activity, downregulate ubiquitin proteasome pathway activity, downregulate serum myostatin levels and/or reduce ActRIIB expression, a receptor for myostatin.

In one nonlimiting embodiment, the composition comprising egg yolk powder is FORTETROPIN administered orally on a daily basis in an amount ranging from about 5 to about 25 grams/day, about 6.6 to about 19.8 grams/day or about 50 to about 300 mg/kg/day, about 80 to about 250 mg/kg/day in humans. In canines, FORTETROPIN is administered orally on a daily basis in an amount ranging from about 200-1000 mg/kg/day, about 300 to about 900 mg/kg/day.

In some embodiments, the composition comprising egg yolk powder is administered at 300 mg/kg daily (one scoop (6600 mg)/22 kg), or the like or a suitable dosage for the weight and characteristics of the mammal. Dosages may be modified for efficacy, for example, may be administered at a higher or lower dosage or administered more than once daily or less than once daily. Mammals may be dosed to the closest ½ scoop, or the like, without underdosing. The composition may be formed in a powder that may be mixed with other food to facilitate ingestion.

However, as will be understood by the skilled artisan upon reading this disclosure, the compositions described herein can be formulated for administration to a subject via any conventional means including, but not limited to, oral, or buccal.

Moreover, the compositions described herein, can be formulated into any suitable dosage form, including but not limited to, aqueous oral dispersions, liquids, gels, syrups, elixirs, slurries, suspensions and the like, for oral ingestion by an individual in need, solid oral dosage forms, controlled release formulations, fast melt formulations, effervescent formulations, lyophilized formulations, tablets, powders, pills, dragees, capsules, delayed release formulations, aqueous liquid dispersions, self-emulsifying dispersions, solid solutions, liposomal dispersions, solid dosage forms, powders, tablets, capsules, pills, delayed release formulations.

Formulations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including glucose, fructose, lactose, sucrose, mannitol, sorbitol, stevia extract, or sucralose; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Formulations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, granules. In other embodiments, the pharmaceutical formulation is in the form of a powder. In still other embodiments, the pharmaceutical formulation is in the form of a tablet. Additionally, formulations described herein may be administered as a single capsule or in multiple capsule dosage form. In some embodiments, the formulation is administered in two, or three, or four, capsules or tablets.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin-based film using technology and machinery known to those in the soft gel industry. The industrial units so formed are then dried to constant weight.

In some embodiments, the formulations may include other medicinal or pharmaceutical agents, carriers, diluents, dispersing agents, suspending agents, thickening agents, adjuvants, such as preserving, stabilizing, wetting or emulsifying agents, solution promoters, and/or buffers. In addition, the formulations can also contain other therapeutically valuable substances.

The formulations described herein can include egg yolk powder and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination (s) thereof. In still other aspects, using standard coating procedures, a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Formulations including egg yolk powder, as described herein, may be manufactured in a conventional manner, such as, by way of example only, by means of conventional mixing, dissolving, granulating, dragee-making, levigating, emulsifying, encapsulating, entrapping or compression processes.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Binders imparting cohesive qualities may also be used. Examples include, but are not limited to, alginic acid and salts thereof; cellulose derivatives such as carboxymethylcellulose, methylcellulose, hydroxypropylmethylcellulose, hydroxyethylcellulose, hydroxypropylcellulose, ethylcellulose, and microcrystalline cellulose; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose, glucose, dextrose, molasses, mannitol, sorbitol, xylitol, and lactose; a natural or synthetic gum such as acacia, tragacanth, ghatti gum, mucilage of isapol husks, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder.

Formulators skilled in art can determine the binder level for the formulations, but binder usage level of up to 70% in tablet formulations is common.

Compositions may further comprise carriers of relatively nontoxic chemical compounds or agents that facilitate the incorporation of a compound into cells or tissues. Nonlimiting examples include binders, suspending agents, disintegration agents, filling agents, surfactants, solubilizers, stabilizers, lubricants, wetting agents, diluents, and the like. Suitable carriers for use in solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Dispersing agents and/or viscosity modulating agents include materials that control the diffusion and homogeneity of a compound through liquid media or a granulation method or blend method. In some embodiments, these agents also facilitate the effectiveness of a coating or eroding matrix. Nonlimiting examples of diffusion facilitators/dispersing agents include hydrophilic polymers, electrolytes, a Tween, PEG, polyvinylpyrrolidone, and carbohydrate-based dispersing agents such as hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers, block copolymers of ethylene oxide and propylene oxide; and poloxamines, tetrafunctional block copolymers derived from sequential addition of propylene oxide and ethylene oxide to ethylenediamine, polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents that are particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

Compositions of the present invention may further comprise diluents used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose; dibasic calcium phosphate, dicalcium phosphate dihydrate; tricalcium phosphate, calcium phosphate; anhydrous lactose, spray-dried lactose; pregelatinized starch, compressible sugar; mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; sodium chloride; inositol, bentonite, and the like.

Compositions may further comprise an enteric coating, a substance that remains substantially intact in the stomach but dissolves and releases the egg yolk powder in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

In addition, the compositions may comprise an erosion facilitator, a material that controls the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

Filling agents including compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like can also be included in the compositions. Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In addition, flavoring agents and/or sweeteners can be used in the compositions and may include acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

The compositions may further comprise lubricants and/or glidants that prevent, reduce or inhibit adhesion or friction of materials. Nonlimiting examples of lubricants include stearic acid, calcium hydroxide, talc, sodium stearyl fumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG-4000) or a methoxypolyethylene glycol, sodium oleate, sodium benzoate, glyceryl behenate, polyethylene glycol, magnesium or sodium lauryl sulfate, colloidal silica, a starch such as corn starch, silicone oil, a surfactant, and the like.

Plasticizers, compounds used to soften the microencapsulation material or film coatings to make them less brittle may also be included in the compositions. Examples of suitable plasticizers include, but are not limited to, polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

The compositions may further comprise solubilizers such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

In addition, the compositions my comprise stabilizers such as antioxidation agents, buffers, acids, preservatives and the like.

Suitable suspending agents for use in solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants including compounds such as sodium lauryl sulfate, sodium docusate, Tweens, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide and the like may also be included. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

Viscosity enhancing agents including, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof may also be included.

In addition, wetting agents including compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like may be included in these compositions.

In some embodiments, solid dosage forms, e.g., tablets, capsules, are prepared by mixing the egg yolk powder described herein, with one or more pharmaceutical excipients to form a bulk blend composition. When referring to these bulk blend compositions as homogeneous, it is meant that the particles of egg yolk powder, are dispersed evenly throughout the composition so that the composition may be readily subdivided into equally effective unit dosage forms, such as tablets, pills, and capsules.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., "The Theory and Practice of Industrial Pharmacy" (1986).

It should be appreciated that there is considerable overlap between additives used in the solid dosage forms described herein. Thus, the above-listed additives should be taken as merely exemplary, and not limiting, of the types of additives that can be included.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials which sufficiently isolate the compound from other non-compatible excipients. Materials compatible with the egg yolk powder are those that delay the release of the egg yolk powder in vivo.

In other embodiments, the formulations described herein, which include the egg yolk powder, are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734.

In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components. The enteric coated oral dosage form may also be a capsule (coated or uncoated) containing pellets, beads or granules of the solid carrier or the composition.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating for the methods and compositions described herein to achieve delivery to the lower gastrointestinal tract.

In some embodiments, formulations are provided that include particles of egg yolk powder described herein and at least one dispersing agent or suspending agent for oral administration to a subject. The formulations may be a powder and/or granules for suspension, and upon admixture with water, a substantially uniform suspension is obtained. Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of egg yolk powder, the liquid dosage forms may include additives, such as: (a) disintegrating agents; (b) dispersing agents; (c) wetting agents; (d) at least one preservative, (e) viscosity enhancing agents, (t) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regards to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

In one nonlimiting embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the formulations described herein can be self-emulsifying drug delivery systems (SEDDS). Emulsions are dispersions of one immiscible phase in another, usually in the form of droplets. Generally, emulsions are created by vigorous mechanical dispersion.

SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563.

Buccal formulations that include egg yolk powder may be administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the egg yolk powder, and any other components that may be present in the buccal dosage unit. Generally, the polymeric carrier comprises hydrophilic (water-soluble and water-swellable) polymers that adhere to the wet surface of the buccal mucosa. Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

In certain embodiments, delivery systems for pharmaceutical compounds may be employed, such as, for example, liposomes and emulsions. In certain embodiments, compositions provided herein can also include a mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

The invention is further illustrated by the following example, which should not be construed as further limiting. The contents of all references, pending patent applications, and published patents cited throughout this application are hereby expressly incorporated by reference.

EXAMPLE

Figure 2:
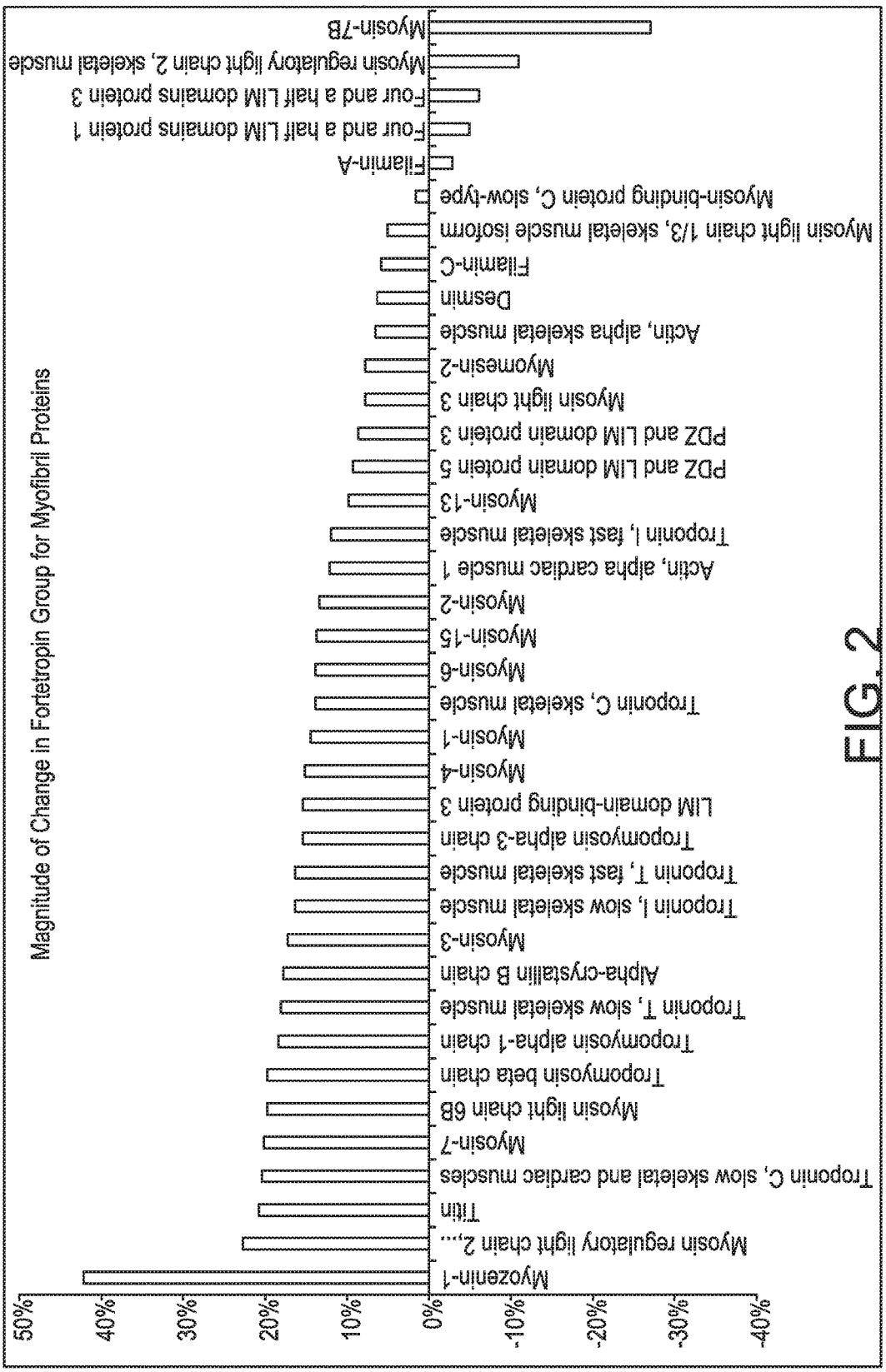
FIG. 2 shows results comparing myofibril proteins fractional synthesis in older adults receiving FORTETROPIN versus cheese powder for 21 days.
Figure 3:
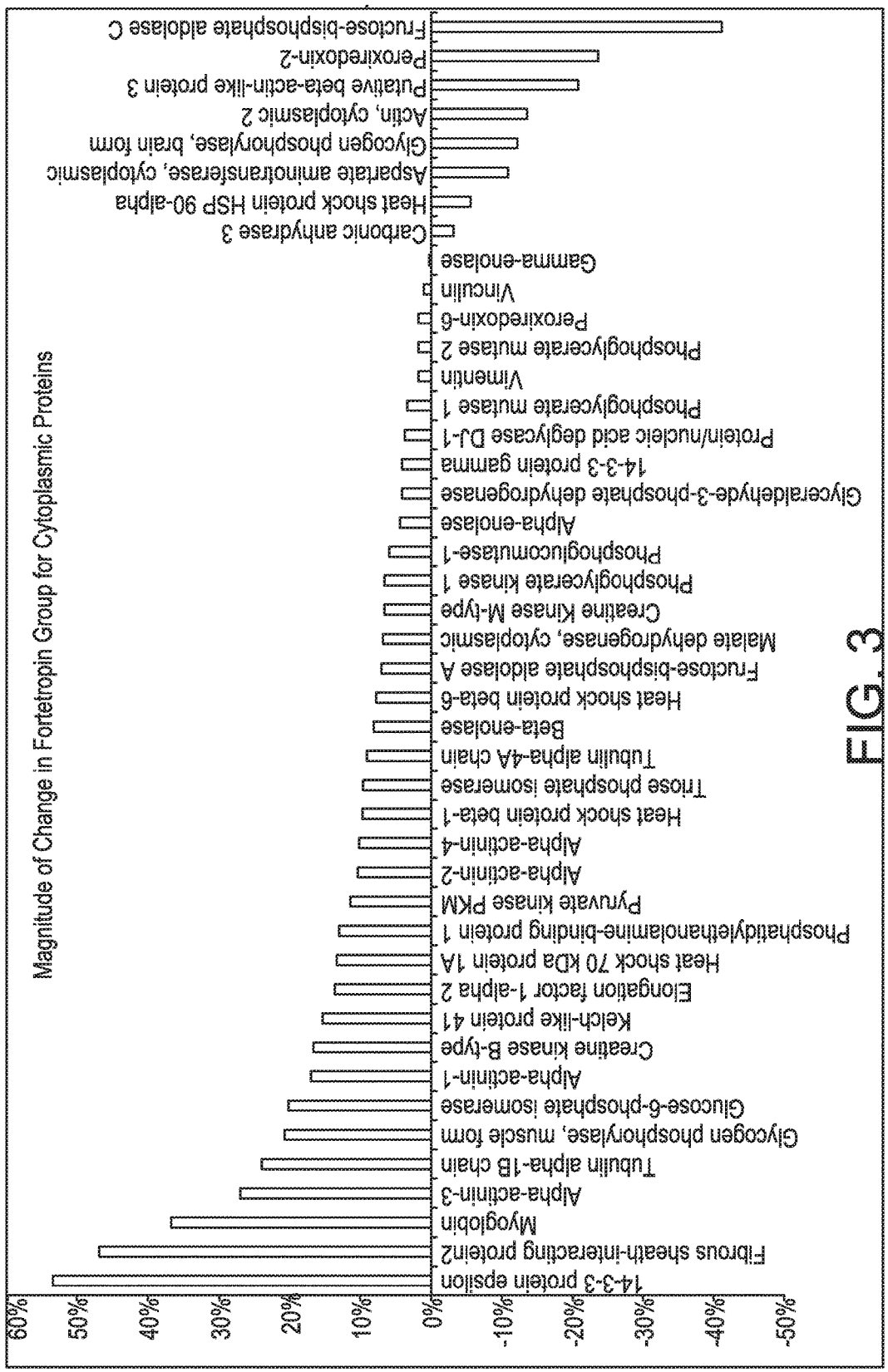
FIG. 3 shows results comparing cytoplasmic proteins fractional synthesis in older adults receiving FORTETROPIN versus cheese powder for 21 days.
Figure 4:
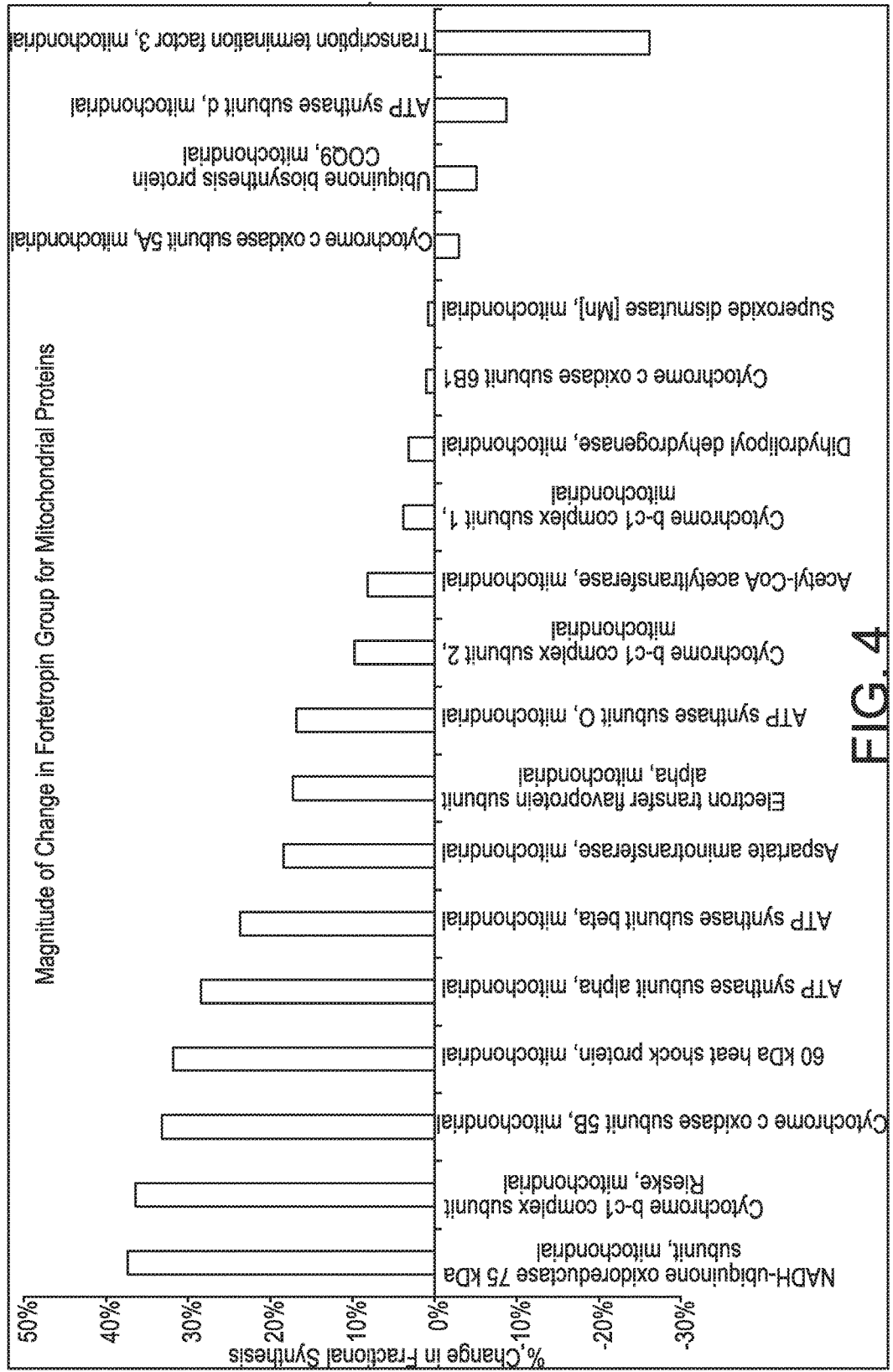
FIG. 4 shows results comparing mitochondrial proteins fractional synthesis in older adults receiving FORTETROPIN versus cheese powder for 21 days.
Figure 5:
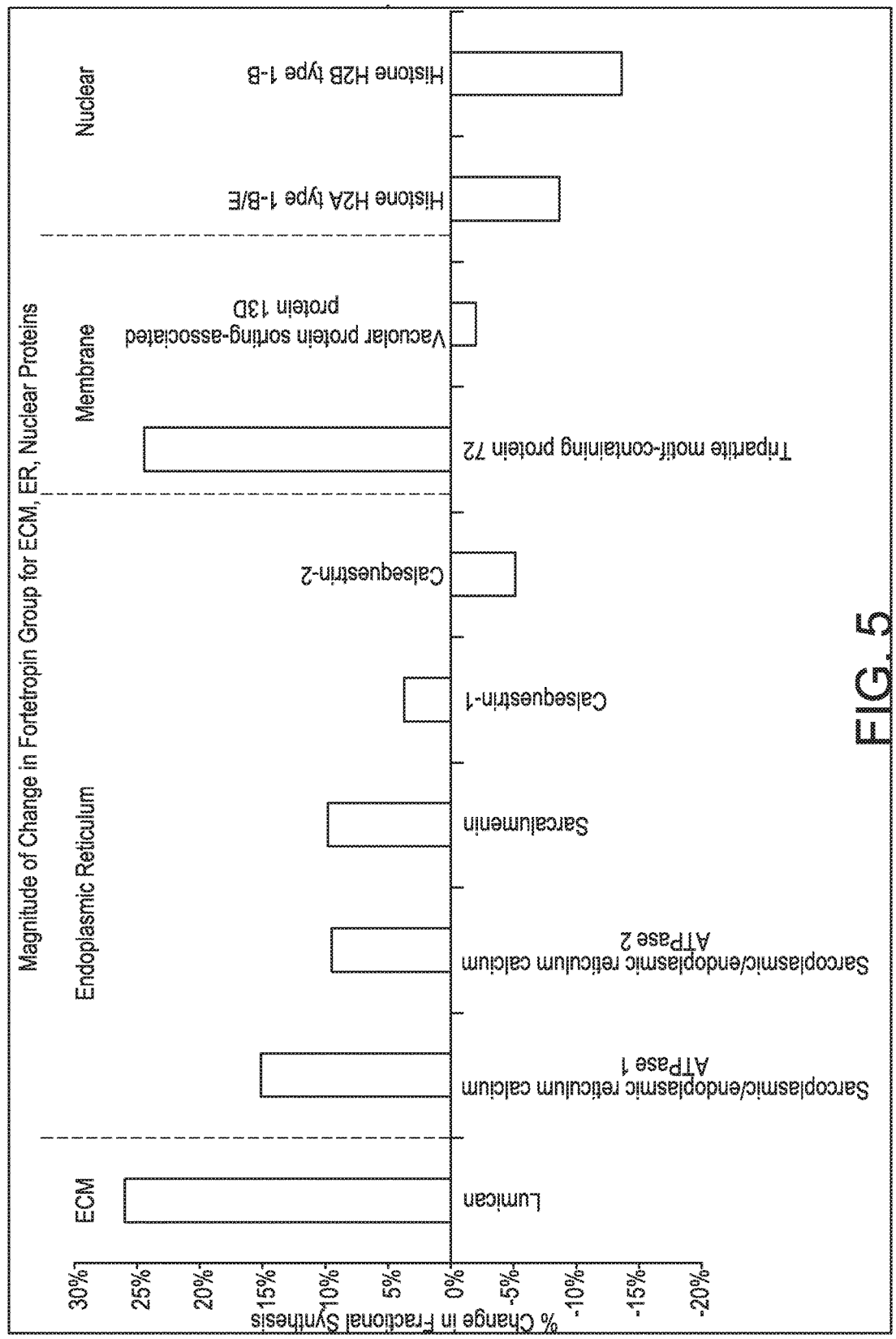
FIG. 5 shows results comparing membrane proteins fractional synthesis in older adults receiving FORTETROPIN versus cheese powder for 21 days.

One benefit of embodiments of the present invention is the effect of egg yolk powder supplementation on the FSR of muscle proteins in men and women between 60 and 75 years old, or of different ages, or the like. In 10 men (n=6) and women (n=4) between 60 and 75 years old, with a BMI between 23 and 29, ingestion of FORTETROPIN (compared with placebo) for 21 days resulted in an increase in the fractional synthetic rate of skeletal muscle proteins as compared to 10 men (n=4) and women (n=6) treated with cheese powder. Design of this FSR study is depicted in FIG. 1. As shown in FIGS. 2 through 4, the average fractional synthesis of a majority of skeletal muscle proteins in several gene ontologies was statistically significantly higher in the FORTETROPIN group (33/38 myofibril proteins (see FIG. 2), 36/44 cytoplasmic proteins (See FIG. 3) and 15/19 mitochondrial proteins (see FIG. 4)). The overall magnitude of increase was 15% indicating a stimulatory effect of the egg yolk powder composition on muscle protein synthesis. Further, these effects were independent of gender or base line muscle mass of the subjects.

Subjects:

The study was comprised of 10 control subjects of 4 men and 6 women and 10 FORTETROPIN subjects of 6 men and 4 women with an average age of 66.35±4.45 years.

Dosing with $^2H_2O$:

All subjects in this study consumed approximately 100-150 ml of 70% $^2H_2O$, divided into two to three 50 ml doses for 21 consecutive days. On the first day of dosing, subjects remained at a clinical site for the initial bolus doses. During the initial four days, each subject drank 150 ml of $^2H_2O$ divided into 50 ml doses consumed at least 3 hours apart, at approximately 9:00 AM, 1:00 PM, and 5:00 PM. This is a bolus dose to increase body water enrichment with $^2H_2O$ rapidly to isotopic steady state (between 1.5% and 2% enrichment). The subjects then continued to consume 100 ml of 70% $^2H_2O$ divided into 2 doses each day of 50 ml (morning and evening) for the remaining 17 days of methods to remain at steady state.

D3-Creatine Dilution for Muscle Mass:

A 30 mg capsule of D3-creatine was swallowed by each subject three days prior to initiation of FORTETROPIN treatment and the first day of $^2H_2O$ dosing. Subjects did not need to be in the fasted condition for this dose. Three days after the dose of D3-creatine, a morning fasted urine sample was collected. Subjects were told to void upon waking and the second void was collected. No food was consumed until the second urine void was collected. The urine sample was frozen as soon as possible. Muscle mass, and in particular an increase in muscle mass, was used as a variable in examination of the response to FORTETROPIN.

Saliva:

Saliva samples were collected to measure $^2H_2O$ enrichment on days 4, 7, 14 and 21. The enrichment of body water was used to calculate muscle protein FSR.

Muscle Biopsy:

After 21 days of treatment with FORTETROPIN, a micro muscle biopsy was collected on each subject midway between the patella and greater trochanter from the vastus lateralis. About 15 mg of tissue was obtained. Muscle sample were removed from the needle, placed in a plastic storage vial and frozen rapidly in liquid nitrogen. Samples were stored in a −70° C. freezer in accordance with exemplary embodiments.

Treatment:

Subjects were provided and asked to consume three packets of FORTETROPIN powder or placebo (isocaloric amount of cheddar cheese, 1.5 oz) at 9:00 PM each evening, or the like.

Blood Samples:

Two blood samples were collected from each subject; one at baseline (study day −3) and one exactly 12 hours after the final dose of FORTETROPIN or placebo was consumed. Blood samples were frozen immediately and stored in a −40° C. freezer for later analysis of circulating myostatin levels. Height was measured on each subject and body weight was measured weekly.

Statistical Power:

Twenty (20) evaluable subject (10 in the FORTETROPIN arm and 10 in the placebo arm) were required to provide 80% power with a two-sided alpha of 0.05 to demonstrate the superiority of FORTETROPIN versus placebo with respect to the primary endpoint (muscle protein fractional synthesis rate). This estimate assumes a within group standard deviation (SD) of 0.25%/hr, with no change in FSR in the placebo group, and a 0.30%/hr increase with FORTETROPIN treatment.

While the foregoing is directed to embodiments of the present invention, other and further embodiments of the invention may be devised without departing from the basic scope thereof. For example, although numerous embodiments having various features have been described herein, combinations of such various features in other combinations not discussed herein are contemplated within the scope of embodiments of the present invention.

What is claimed is:

1. A method for inhibiting or reversing sarcopenia in a mammal, said method comprising orally administering to the mammal on a daily basis a composition comprising egg yolk powder in an amount ranging from about 50 to about 300 mg/kg/day of said composition.

2. The method of claim 1 wherein the mammal is an older adult.

3. The method of claim 1 wherein the composition comprises a fertilized egg yolk derived product.

4. The method of claim 3 wherein the fertilized egg yolk derived product is produced via high pressure pasteurization and freeze drying of at least a portion of an egg.

5. The method of claim 1 wherein the egg yolk powder is administered in an amount effective to upregulate mTor pathway activity, downregulate ubiquitin proteasome pathway activity, downregulate serum myostatin levels and/or reduce ActRIIB expression.

6. The method of claim 1 wherein the composition comprises avian follistatin.

* * * * *